(12) United States Patent
Chow et al.

(10) Patent No.: US 7,569,595 B2
(45) Date of Patent: Aug. 4, 2009

(54) 2-((2-THIOXO-2,3-DIHYDRO-1H-IMIDAZOL-4-YL)METHYL)-3,4-DIHYDRONAPHTHALEN-1(2H)-ONE

(75) Inventors: Ken Chow, Newport Coast, CA (US); Todd M. Heidelbaugh, Fountain Valley, CA (US); Daniel W. Gil, Corona Del Mar, CA (US); Michael E. Garst, Newport Beach, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/034,303

(22) Filed: Feb. 20, 2008

(65) Prior Publication Data

US 2008/0146635 A1 Jun. 19, 2008

Related U.S. Application Data

(60) Division of application No. 11/368,990, filed on Mar. 6, 2006, now Pat. No. 7,358,269, which is a continuation-in-part of application No. 10/437,807, filed on May 14, 2003, now Pat. No. 7,091,232, which is a continuation-in-part of application No. 10/153,328, filed on May 21, 2002, now abandoned.

(51) Int. Cl.
*A61K 31/4164* (2006.01)
*C07D 233/04* (2006.01)

(52) U.S. Cl. ............ 514/386; 548/316.4; 548/323.5; 514/385

(58) Field of Classification Search ........... 548/316.4, 548/323.5; 514/385, 386
See application file for complete search history.

(56) References Cited

U.S. PATENT DOCUMENTS

| | | | |
|---|---|---|---|
| 3,996,366 A | 12/1976 | Baker et al. | |
| 4,798,834 A | 1/1989 | Merritt et al. | |
| 4,798,843 A * | 1/1989 | Kruse .................. | 514/392 |
| 4,977,174 A | 12/1990 | Stein et al. | |
| 5,441,970 A | 8/1995 | Reitz et al. | |
| 5,648,373 A | 7/1997 | Winkler et al. | |
| 5,861,420 A | 1/1999 | Reitz et al. | |
| 5,929,103 A | 7/1999 | Yoon et al. | |
| 5,932,742 A | 8/1999 | Yoon et al. | |
| 6,043,373 A | 3/2000 | Yoo et al. | |
| 6,313,172 B1 | 11/2001 | Chow et al. | |
| 6,465,486 B1 | 10/2002 | Baxter et al. | |
| 6,534,542 B2 | 3/2003 | Chow et al. | |
| 6,545,182 B2 | 4/2003 | Chow et al. | |
| 7,091,232 B2 | 8/2006 | Chow et al. | |
| 7,141,597 B2 * | 11/2006 | Chow et al. ........... | 514/392 |
| 7,183,305 B2 | 2/2007 | Dolby et al. | |
| 7,276,522 B2 * | 10/2007 | Heidelbaugh et al. ... | 514/314 |
| 7,345,065 B2 * | 3/2008 | Gil et al. ............. | 514/365 |
| 7,358,269 B2 * | 4/2008 | Chow et al. ........... | 514/386 |

| | | |
|---|---|---|
| 2002/0094998 A1 | 7/2002 | Burke et al. |

FOREIGN PATENT DOCUMENTS

| | | |
|---|---|---|
| WO | 1 499 485 | 2/1978 |
| WO | WO 92/00073 | 1/1992 |
| WO | WO 99/28300 | 6/1999 |
| WO | WO 01/00586 | 1/2001 |
| WO | WO 02/36162 A2 | 5/2002 |
| WO | WO 03/099795 | 12/2003 |

OTHER PUBLICATIONS

Berque et al.: "Allyltitanates in Stereospecific Additions to Chiral d-Lactol: Efficient Enantioselective Route to a Potential Precursor of the C1-C9 Portion of tylonide" J. Med. Chem., 1999, 373.
Burke et al (2002): STN International HCAPLUS database, Columbus (OH), accession No. 2002: 353314.
Ciufolini et al.: "The Total Synthesis of Cystodytins" J. Amer. Chem. Soc., 1991, 113, 8016.
Conklin et al.: Substitution of Three Amino Acids Switches Receptor Specificity of Gqα to That of Glα Nature, 1993, pp. 274-274, 363.
Cook et al.: "Silicon In Synthesis. Vinyltrimethylsilane, a Convenient Ethylene Equivalent For The Synthesis of Vinyl Aryl Sulfides, Vinyl Aryl Sulfoxides, thiosilylketene Acetals, and Fused Cyclopentenones" J. Org. Chem., 1980, 45, 1046.
Corey et al.: "A New Chiral Catalyst For The Enantioselective Synthesis of Secondary Alcohols And deuterated Primary Alcohols By Carbonyl Reduction" Tetrahedron Lett., 1989, 30, 6275.
Dirig et al.: "Characterization of variables defining hindpaw withdrawal latency evoked by radiant thermal stimuli" J. Neurosci. Methods, 1997, p. 183-191, 76.
Dixon et al.: "Efficient Analysis Of Experimental Observations" Ann. Rev. Pharmacol. Toxicol., 1980, p. 441-462, 20.
Hargreaves et al.: "A New And Sensitive Method For Measuring Thermal Nociception In cutaneous Hyperalgesia" Pain, 1988, p. 77-88, 32.
Horne et al.: "A Two-Step Synthesis of Imidazoles From Aldehydes Via 4-Tosyloxazolines" Heterocycles, 1994, 39, 139.
Hua et al.: "A One-Pot Condensation of Pyrones and Enals. Synthesis of 1H,7H-5a,6,8,9-Tetrahydro-I-oxopyrano[4,3-6][1]benzopyrans" J. Org. Chem. 1997, 62, 6888.

(Continued)

*Primary Examiner*—Golam M Shameem
(74) *Attorney, Agent, or Firm*—Kevin Forrestal

(57) ABSTRACT

A compound of the formula

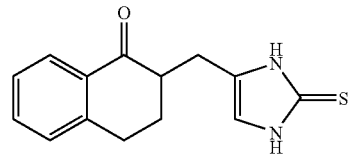

or a pharmaceutically acceptable salt thereof, is disclosed herein. Methods and compositions related thereto are also disclosed.

5 Claims, No Drawings

OTHER PUBLICATIONS

Huang et al.: "The Improved Preparation of 7,8-Dihydro-Quinoline-5(6H)-One and 6,7-Dihydro-5H-1-Pyrindin-5-One" Synthetic Communications, 1998, 28, 1197.

Jackman et al(1949): STN International CAPLUS data base, Columbus, Ohio, Accession No. 1998: 147327.

Jackman et al.: "The Preparation of Some Substituted Thiohydantoins and Thioimidazoles" vol. 70, pp. 2884-2886.

Jennesken et al.: "Flash Vacuum Thermolysis of 5,6,8,9-Tetrahydro-4'-Methylenesprio[7H-benzocycloheptene-7,1'-cyclohexa-2',5'-diene]. The Intermediate Formation of [3,2]orthoparacyclophane" J. Org. Chem. 1986, 51, 2162.

Kim et al.: "An Experimental Model For Peripheral Neuropathy Produced By Segmental Spinal Nerve Ligation In the Rat" Pain, 1992, p. 355-363, 150.

Kim et al.: "A Facile Synthesis of α-Chloro Enones By Oxidative Chlorination" Synthesis, 1993, 283.

Kowalski et al.: "α-Keto dianion Precursors via Conjugate Additions to Cyclic α-Bromo Enones" J. Org. Chem., 1982, 47, 5088.

Lemke et al.: "Synthesis of 5,6-Dihydro-8(7H)-quinolinone Thiosemicarbazones as potential Antitumor Agents" J. Org. Chem., 1977, 20, 1351.

Mancuso: "Activated Dimethyl Sulfoxide: Useful Reagents For Synthesis" Synthesis, 1981, p. 165.

Messier et al.: "High Throughput Assays of Cloned Adrenergic, Muscarinic, Neurokinin, and Neurotrophin receptors in Living Mammalian Cells" Pharmacol. Toxicol., 1995, p. 183-191, 76.

Molina et al.: "Vinyliminophosphorane-Mediated Preparation of 2-Arylquinoline and 4-Aryl-1-azaanthraquinone Derivatives. X-Ray Crystal Structure of 1,2-Dihydro-3H-indazolo[2,3-a]quinolin-4-one" Tetrahedron, 1995, 51, 1265.

Organ et al.: "Ni-Catalyzed Cross Coupling of Alkoxide-Containing Vinyl Halides With Grignard Reagents. A "One-Pot" Synthesis of 2-[(Trimethylsilyl)methyl]-2-propen-1-yl Acetate" J. Org. Chem., 1977, 62, 1523.

Sosa et al.: "Synthesis of Axinohydantoins" J. Org. Chem., 2002, 4498-4500, 67.

Woods et al.: "Syntheses with Dihydroresorcinol Mono Ethyl Ether: 3-Alkyl-Δ2-cyclohexenones" J. Amer. Chem. Soc., 1949, 71, 2028-2031.

Xavier et al.: "(S)-Tetrahydro-1-Methyl-3,3-Diphenyl-1H,3H-Pyrrolo-[1,2-c][1,3,2]Oxazaborole-Borane Complex (Boron, Trihydro(Tetrahydro-1-methyl-3,3-diphenyl-1H-pyrrolo-[1,2-c][1,3,2]oxazaborole-N7)-, [1-4-(3aS-cis)]-)" Organic Synthesis, 1996, 74, 50.

Yoon et al (1998): STN International CAPLUS data base, Columbus, Ohio, Accession No.: 1998: 147327.

* cited by examiner

2-((2-THIOXO-2,3-DIHYDRO-1H-IMIDAZOL-4-YL)METHYL)-3,4-DIHYDRONAPHTHALEN-1(2H)-ONE

CROSS-REFERENCE TO RELATED APPLICATIONS

The present application is a divisional of application Ser. No. 11/368,990, filed on Mar. 6, 2006, now U.S. Pat. No. 7,358,259 which is continuation-in-part of application serial number 10/437,807 filed on May 14, 2003, which is a continuation-in-part of application Ser. No. 10/153,328 filed on May 21, 2002 now abandoned.

BACKGROUND OF THE INVENTION

Background

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha-2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2002 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. No. 4,798,843 describes (phenyl)-imidazole-2-thiones and substituted (phenyl)-imidazole-2-thiones.

U.S. Pat. Nos. 6,545,182 and 6,313,172 describe phenylmethyl-(2hydroxy)ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of alpha$_{2B}$ adrenergic receptors. In a different biological or pharmaceutical context United States Published Application 20020094998, published on Jul. 18 2002 and claiming priority of U.S. Provisional Application No. 6/0244,850 discloses a compound without assigning the proper stereochemistry to it, which corresponds to two compounds described in the present application with the proper stereochemistry.

DESCRIPTION OF THE INVENTION

One embodiment is a compound of Formula 1

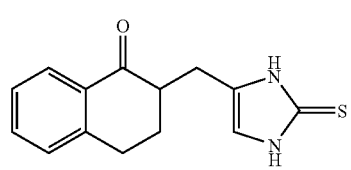

Formula 1 or a pharmaceutically acceptable salt thereof.

Another embodiment is a composition comprising a racemic mixture of the compound of Formula I.

Another embodiment is a composition consisting essentially of a substantially pure racemic mixture of the compound of Formula I.

Another embodiment is a composition comprising the S-enantiomer of the compound of Formula I.

Another embodiment is a composition consisting essentially of a substantially pure S-enantiomer of the compound of Formula I.

Another embodiment is a composition having an enantiomeric excess of an R-enantiomer of the compound of Formula I.

Another embodiment is a composition consisting essentially of a substantially pure R-enantiomer of the compound of Formula I.

Another embodiment is a composition comprising a mixture of enantiomers of the compound of Formula I. having (+) optical activity.

Another embodiment is a composition consisting essentially of a substantially pure (+)-entantiomer of the compound of Formula I.

Another embodiment is a composition comprising a mixture of enantiomers of the compound of Formula I. having (−) optical activity.

Another embodiment is a composition consisting essentially of a substantially pure (−)-entantiomer of the compound of Formula I.

One embodiment is a compound comprising 2-((2-thioxo-2,3-dihydro-1H-imidazol-4-yl)methyl)-3,4-dihydronaphthalen-1(2H)-one, or a pharmaceutically acceptable salt thereof.

Another embodiment is a composition comprising a racemic mixture of said compound.

Another embodiment is a composition consisting essentially of a substantially pure racemic mixture of said compound.

Another embodiment is a composition comprising the S-enantiomer of said compound.

Another embodiment is a composition consisting essentially of a substantially pure S-enantiomer of said compound.

Another embodiment is a composition having an enantiomeric excess of an R-enantiomer of said compound.

Another embodiment is a composition consisting essentially of a substantially pure R-enantiomer of said compound.

Another embodiment is a composition comprising a mixture of enantiomers of said compound having (+) optical activity.

Another embodiment is a composition consisting essentially of a substantially pure (+)-entantiomer of said compound.

Another embodiment is a composition comprising a mixture of enantiomers of said compound having (−) optical activity.

Another embodiment is a composition consisting essentially of a substantially pure (−)-entantiomer of said compound.

Other embodiments are pharmaceutical compositions containing as the active ingredient one or more compounds of Formula 1, the compositions being utilized as medicaments in mammals, including humans, for treatment of diseases and or alleviations of conditions which are responsive to treatment by agonists of alpha$_{2B}$ adrenergic receptors. The compositions containing the compounds disclosed herein are primarily, but not exclusively, used for alleviation of chronic pain and/or allodynia. The compounds have the demonstrable advantageous property that they are specific or selective to alpha$_{2B}$ and/or alpha$_{2C}$ adrenergic receptors in preference over alpha$_{2A}$ adrenergic receptors, and as such have no or only minimal cardiovascular and/or sedatory activity.

It will be readily apparent to those skilled in the art that

Imidazole-2-thiones can undergo tautomeric transformations and can be depicted by the tautomeric formulas shown below. All tautomers of Formula 1 are within the scope of the invention.

TABLE 1

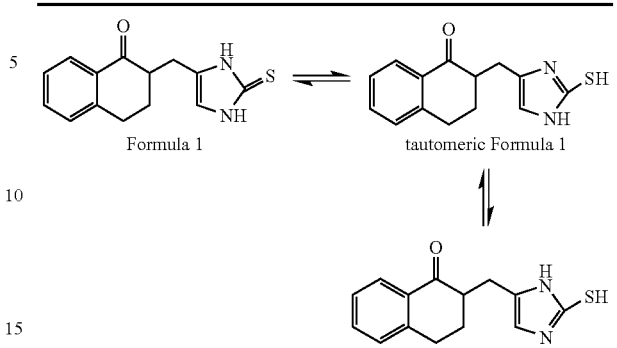

| Compound # | Alpha 2A | EC$_{50}$ (nM) (intrinsic activity) Alpha 2B | Alpha 2C |
|---|---|---|---|
| Compound 1S | NA | 41 (0.83) | NA |

(−) enantiomer

| Compound 1R | NA | 92 (0.79) | NA |

(+) enantiomer

Biological Activity, Modes of Administration

The compounds disclosed herein are agonists of alpha$_2$ adrenergic receptors, particularly they tend to be specific or selective agonists of alpha$_{2B}$ and/or to a lesser extent alpha$_{2C}$ adrenergic receptors, in preference over alpha$_{2A}$ adrenergic receptors. The specific or selective alpha$_{2B}$ and/or to a lesser extent alpha$_{2C}$ agonist activity of the disclosed compounds is demonstrated in an assay titled Receptor Selection and Amplification technology (RSAT) assay, which is described in the publication by Messier et. Al., 1995, Pharmacol. Toxicol. 76, pp. 308-311 (incorporated herein by reference) and is also described below. Another reference pertinent to this assay is Conklin et al. (1993) Nature 363:274-6, also incorporated herein by reference.

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha$_2$ receptors, which normally couple to G$_i$, activate the RSAT response when coexpressed with a hybrid Gq protein that has a G$_i$ receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-ga-lactosidase (5-10 µg), receptor (1-2 µg) and G protein (1-2 µg). 40 µg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37 EC. After washing with phosphate-buffered saline, β-galactosidase enzyme activity is determined by adding 200 µl of the chromogenic substrate (consisting of 3.5 mM o-nitrophenyl-β-D-galactopyranoside and 0.5% nonidet P-40 in phosphate buffered saline), incubating overnight at 30 EC and measuring optical density at 420 nm. The absorbance is a measure of enzyme activity, which depends on cell number and reflects a receptor-mediated cell proliferation. The EC$_{50}$ and maximal effect of each drug at each alpha$_2$ receptor is determined. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors.

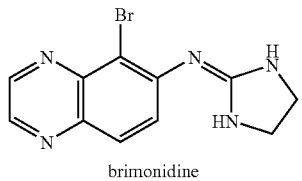

brimonidine

The results of the RSAT assay with several exemplary compounds are disclosed in Table 1 above together with the chemical formulas of these examplary compounds. Each number in the table represents EC$_{50}$ in nanomolar (nM) concentration whereas the number in parenthesis in the table shows the fraction of activity of the appropriate standard which is attained by the tested compound. NA stands for "not active" at concentrations less than 10 micromolar. As is known EC$_{50}$ is the concentration at which half of a given compound's maximal activity is observed.

Generally speaking alpha2 agonists, can alleviate sympathetically-sensitized conditions that are typically associated with periods of stress. These include 1) the increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha2 agonists including alpha2B/2C agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha$_{2B}$ and/or alpha$_{2C}$ adrenergic receptors in preference over alpha$_{2A}$ receptors, if the compound is at least ten (10) times more active towards either alpha$_{2B}$ or towards alpha$_{2C}$ receptors than towards alpha$_{2A}$ receptors. It can be seen from these tables that the disclosed compounds are specific or selective agonists of alpha$_{2B}$ and/or alpha$_{2C}$ adrenergic receptors within the former definition, and in fact have no agonist like activity or only insignificant agonist-like activity on alpha$_{2A}$ receptors.

Thus, the disclosed compounds are useful for treating conditions and diseases which are responsive to treatment by alpha$_{2B}$ and/or alpha$_{2C}$ adrenergic receptor agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the disclosed compounds are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis.

The activity of the disclosed compounds is highly advantageous because the administration of these compounds to mammals does not result in sedation or in significant cardiovascular effects (such as changes in blood pressure or heart rate).

The disclosed compounds act and can be used as a highly effective analgesic, particularly in chronic pain models, with minimal undesirable side effects, such as sedation and cardiovascular depression, commonly seen with other agonists of the $\alpha_2$ receptors.

The disclosed compounds may be administered at pharmaceutically effective dosages. Such dosages are normally the minimum dose necessary to achieve the desired therapeutic effect; in the treatment of chronic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Also disclosed are therapeutic compositions comprising the compounds of Formula 1 and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

Also disclosed are methods for the treatment of pain, particularly chronic pain, through the administration of one or more compounds of Formula 1 or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A$\beta$ and A$\delta$ fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A$\beta$ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain. The following in vivo assays can be employed to demonstrate the biological activity of the compounds.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Effects on Cardiovascular System

To test the effect of the compounds on the cardiovascular system, typically six cynomolgus monkeys are given 500 µg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test show that the compounds of disclosed herein have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitoneally (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

Alleviation of Chronic Pain

A model in accordance with Kim and Chung 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra Xlll down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in approximately 10 to 50% DMSO and given in a volume of 1 ml/kg body weight.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980). The post-drug threshold is compared to the pre-drug threshold and the percent reversal of tactile sensitivity is calculated based on a normal threshold of 15.1 grams. The results are expressed in per cent (%) MPE, where the MPE value reflects the percentage reversal of pain threshold to that of a normal animal (100%).

TABLE 3

Activity of Compounds in Chung Model of Neuropathic Pain (% Pain Reversal ± SEM)
Dose and Route of Administration

| Compd. | 1 µg/kg i.p. | 3 µg/kg i.p. | 10 µg/kg i.p. | 30 µg/kg i.p. | 100 µg/kg i.p. | 300 µg/kg i.p. | 1000 µg/kg i.p. |
|---|---|---|---|---|---|---|---|
| 1S & 1R | 0.8 ± 1.9 | 44 ± 6.3* | 69 ± 15* | 65 ± 11* | 80 ± 9.4* | 81 ± 10* | |
| 1S | 0.7 ± 0.8* | 59 ± 5.8* | 74 ± 6.1* | 69 ± 10* | | | |

| Compd. | 10 µg/kg p.o. | 30 µg/kg p.o. | 100 µg/kg p.o. | 300 µg/kg p.o. | 1000 µg/kg p.o. |
|---|---|---|---|---|---|
| 1S & 1R | 2 ± 0.6 | 81 ± 8.2* | 87 ± 6.1* | 96 ± 4.5* | |

All measurements 30 min following drug administration.
*p value <0.001 compared to pretreatment values.

The results shown in Table 3 illustrate that these compounds significantly alleviate allodynic pain, and based on these test and/or on the compounds ability to activate alpha$_{2B}$ and/or alpha$_{2C}$ adrenergic receptors in preference over alpha$_{2A}$ adrenergic receptors, the compounds are expected to be useful as analgesics to alleviate allodynia and chronic pain.

SPECIFIC EMBODIMENTS, EXPERIMENTAL

EXAMPLE E

Method E: Procedure for Preparation 2-(2-thioxo-2, 3-dihydro-1H-imidazol-4-ylmethyl)-3,4-dihydro-2H-naphthalen-1-one (Compound 1S and Compound 1R)

Column chromatography with 5-7% MeOH:CHCl$_3$ afforded ~0.9 g (45%) of a solid comprising 2-(1H-imidazol-4-ylmethylene)-3,4-dihydro-2H-naphthalen-1-one (Intermediate E4). The synthesis of 2-(2-thioxo-2,3-dihydro-1H-imidazol-4-ylmethyl)-3,4-dihydro-2H-naphthalen-1-one (Intermediate E5) was completed by subjecting the imidazole (Intermediate E4) to the conditions described in Method A for Example A for the conversion to the thione (Intermediate E5 ).

$^1$H NMR (500 MHz, DMSO-d$^6$ w/TMS) δ 11.9 (s, 1H), 11.7 (s, 1H), 7.88 (d, J=7.5 Hz, 1H), 7.57-7.54 (m, 1H),

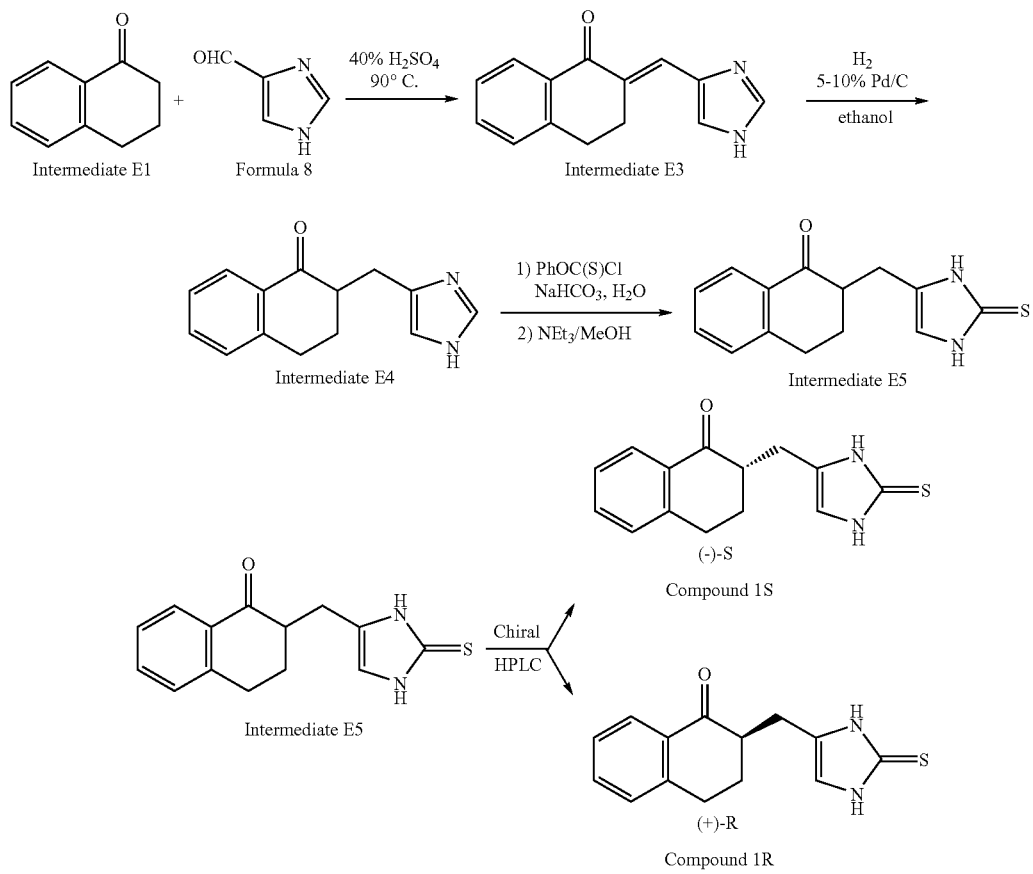

1-Tetralone (commercially available from Aldrich) (Intermediate E1, 1.24 g, 8.5 mmol) and 4,5-imidazole carboxaldehyde (Formula 8, (0.82 g, 8.5 mmol) were added to 8.5 mL of a 40% solution of H$_2$SO$_4$. The solution was heated for 24 h at 90 EC. After cooling to rt, the reaction was made basic with excess concentrated NH$_4$OH. The mixture was extracted twice with THF. The organic layers were combined and washed with brine. The organic layer was separated and dried over Na$_2$SO$_4$. The mixture was filtered and the filtrate concentrated under reduced pressure to afford ~2.2 g of a yellow solid 2-(1H-imidazol-4-ylmethylene)-3,4-dihydro-2H-naphthalen-1-one (Intermediate E3). The crude product (Intermediate E3) was suspended in ethanol (100 mL) and a palladium on carbon catalyst (10%, 0.27 g) added. The mixture was shaken in a Parr hydrogenator apparatus while under 40 psi of hydrogen. After 19 h the reaction mixture was filtered through Celite and the filtrate concentrated under reduced pressure.

7.37-7.34 (m, 2H), 6.58 (s, 1H), 3.08-2.97 (m, 2H), 2.86-2.85 (m, 1H), 2.43 (dd, J=9.0, 6.0 Hz, 1H), 2.08 (dd, J=4.0, 4.5 Hz, 1H), 1.1 (brs, 1H).

The racemic 2-(2-thioxo-2,3-dihydro-1H-imidazol-4-ylmethyl)-3,4-dihydro-2H-naphthalen-1-one (Intermediate E5 ) was separated by chiral HPLC using a ChiralPak AD 4.6×220 mm (Daicel Chem. Ind. Ltd.) with isocratic flow 1.2 mL/m, 10% isopropyl alcohol in acetonitrile mobile phase at 20 EC and UV 210 nm. The first peak with 6.5 min. retention time gave Compound 1S (−) S with [α]$_D^{20}$−66.4 (c=0.57 in 9% DMSO:MeOH). The second fraction at 14.0 min. gave Compound 1R (+) R with [α]$_D^{20}$+61.9 (c=0.63 in 10% DMSO:MeOH). The absolute stereochemistry of Compounds 1S and 1R, as shown in the scheme, was assigned by derivatization followed by X-ray crystallography.

What is claimed is:

1. A method of alleviating pain in a mammal in need of such activation by administering to the mammal a pharmaceutical composition containing a therapeutically effective dose of the following compound

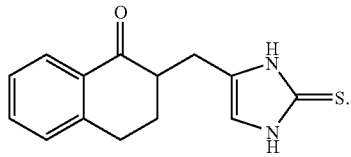

2. A method in accordance with claim 1 where the pharmaceutical composition is administered to the mammal to alleviate chronic pain.

3. A method in accordance with claim 1 where the pharmaceutical composition is administered to the mammal to alleviate allodynia.

4. A method in accordance with claim 1 where the pharmaceutical composition is administered orally.

5. A method in accordance with claim 1 where the pharmaceutical composition is administered intraperitionally.

* * * * *